(12) United States Patent
Sulamanidze et al.

(10) Patent No.: US 8,192,462 B2
(45) Date of Patent: Jun. 5, 2012

(54) SURGICAL SUTURE MATERIAL AND METHOD FOR THE APPLICATION THEREOF

(76) Inventors: Marlen Andreevich Sulamanidze, Moscow (RU); Georgiih Marlenovich Sulamanidze, Moscow (RU)

(*) Notice: Subject to any disclaimer, the term of this patent is extended or adjusted under 35 U.S.C. 154(b) by 717 days.

(21) Appl. No.: 12/300,401

(22) PCT Filed: May 16, 2006

(86) PCT No.: PCT/RU2006/000241
§ 371 (c)(1),
(2), (4) Date: Nov. 11, 2008

(87) PCT Pub. No.: WO2007/133103
PCT Pub. Date: Nov. 22, 2007

(65) Prior Publication Data
US 2009/0210003 A1  Aug. 20, 2009

(51) Int. Cl.
*A61B 17/04* (2006.01)
(52) U.S. Cl. ........ 606/228; 606/144; 606/148; 606/222; 606/224
(58) Field of Classification Search .......... 606/222–228, 606/144
See application file for complete search history.

(56) References Cited

U.S. PATENT DOCUMENTS

| | | | |
|---|---|---|---|
| 5,053,047 A | 10/1991 | Yoon | |
| 5,342,376 A | 8/1994 | Ruff | |
| 5,374,268 A | 12/1994 | Sander | |
| 5,549,629 A * | 8/1996 | Thomas et al. | 606/223 |
| 5,792,180 A * | 8/1998 | Munoz | 606/223 |
| 5,928,268 A * | 7/1999 | Butwell et al. | 606/222 |
| 5,931,855 A | 8/1999 | Buncke | |
| 6,145,714 A * | 11/2000 | Flavin | 223/102 |
| 2003/0074023 A1* | 4/2003 | Kaplan et al. | 606/228 |
| 2003/0149447 A1* | 8/2003 | Morency et al. | 606/228 |
| 2004/0054375 A1* | 3/2004 | Houser et al. | 606/144 |

(Continued)

FOREIGN PATENT DOCUMENTS

EP 0205811 12/1986
(Continued)

OTHER PUBLICATIONS

Semenov G.M. et al. Khirurgichesky shov, Piter, St. Petersburg, 2001, p. 70.

(Continued)

*Primary Examiner* — Corrine M McDermott
*Assistant Examiner* — Alexander Orkin
(74) *Attorney, Agent, or Firm* — Bachman & LaPointe, P.C.

(57) ABSTRACT

A surgical suture material and a method to the use thereof are represented by different needles and surgical threads. The main embodiments comprises a needle (6), consisting of two needles (7, 8) jointed by a temporary connection having a tetrahedral, diamond or another shape in such a way that a single needle point (9) is formed, and a surgical thread (10) provided with shaped design projections embodied on the thread surface in the form of notches. The shaped design of the notches has a very important significance since it makes it possible to provide a reliable linkage with soft tissues and to forcedly holding the soft tissues when force actions are applied thereto. The method consists in introducing, during a surgical intervention, the twin needle in one puncture at a small depth, wherein the needle is divided into two needles, and in leading each needle along a required contour. The surgical suture material can be extensively used for surgical and cosmetic interventions.

1 Claim, 6 Drawing Sheets

U.S. PATENT DOCUMENTS

2005/0203576 A1 9/2005 Sulamanidze et al.
2008/0051833 A1* 2/2008 Gramuglia et al. ........... 606/222

FOREIGN PATENT DOCUMENTS

| EP | 1075843 | 2/2005 |
| GB | 1091282 | 11/1967 |
| RU | 2186536 | 8/2002 |
| RU | 2195186 | 12/2002 |
| SU | 825066 | 4/1981 |
| SU | 1745214 | 7/1992 |
| WO | 03/001979 | 1/2003 |
| WO | 2006011824 | 2/2006 |

OTHER PUBLICATIONS

Egiev V.N. et al. Khirurgichesky shov, medpraktika-M, M., 2001, p. 79.

European Search Report for EP06824414, dated Apr. 6, 2010.

* cited by examiner

SURGICAL SUTURE MATERIAL AND METHOD FOR THE APPLICATION THEREOF

BACKGROUND OF THE INVENTION

The invention relates to medicine, to appliances and methods of carrying out surgical operations and manipulations. In particular, the invention relates to medicinal materials used in surgery in plastic cosmetic operations.

Surgical suture material, that is, needles with threads for sewing up the edges of wounds in surgical operations, threads for cosmetically tightening soft tissues with needles of different forms or without them, but with special devices for introducing the needles into the tissues, are known:

Application PCT/RU2004/000252 of Jun. 30, 2004.
EP 0205811 A1 of Dec. 30, 1986.
RU 2186536 C2
U.S. Pat. No. 5,342,376 of Aug. 30, 1994.

The needles are manufactured from metal, most frequently steel, they can be straight or bent around their circumference, or have another shape. At one end there is a point, while at the other end there is an eye for inserting a surgical suture thread. For sewing up the edges of wounds, atraumatic needles have been used during the past decades, which lack the eye, while the suture thread is fastened to the needle by an industrial method, which allows the surgeon to use disposable sterile suture material, and most importantly a needle which does not comprise a bulky eye and a double thread. Such a needle marginally traumatizes the soft tissues when the needle with the thread is passed therethrough.

The needle can be double-pointed, and the thread can be connected to it in the centre or at the extension. The shape of the needle is determined by the method of its application in the surgical operation.

The threads, which are atraumatically connected with the needles, can be manufactured from different non-absorbing or absorbing materials, with different thickness and strength, integrally (in one filament), woven, spun, or coated with a different material.

The general characteristics of surgical needles are: strength, a smooth surface, biological inertness. They must penetrate the skin easily and pass freely through the subcutaneous tissues. For sewing up open wounds in a continuous suture process, suture materials with bent needles are used, straight needles are not useful in this case.

Surgical needles can be smooth, coarse, and can also have protrusions arranged at an angle on their surface.

Methods for arranging surgical sutures for sewing up wounds or sewing subcutaneous tissues are known: interrupted sutures, mattress sutures, continuous sutures, etc. The sewing of subcutaneous tissues is carried out in the open wound for sewing its edges up, without incisions of the skin through punctures for tightening the soft tissues, and through short incisions of the skin when an endoscopic operation is carried out. The latter two approaches are usually employed in aesthetic surgery for sewing and tightening of ptotic subcutaneous tissues and fastening them in a new and higher position, which renders a better aesthetic result. These operations and manipulations are easily and well carried out only with suture threads with double-pointed needles.

The known suture material with protrusions for sewing up the edges of wounds with perpendicular single stitches (U.S. Pat. No. 5,053,047 of Oct. 1, 1991), and also for a continuous subcutaneous and intracutaneous sewing up of wound edges, has some negative properties, which prevent the implementation of quality surgery.

In sewing up open wounds with the method claimed in US WO-A-98/52473 of May 21, 1997, the skin edges of the wound are positioned badly with respect to each other if only subcutaneous sutures are applied. If, however, such sutures are applied intracutaneous, they become visible, and, since the claimed method for sewing wounds does not provide for a removal of the sutures after the wound is healed, this factor does not allow to obtain an aesthetically acceptable post-operational scar. A further downside of said method are the high costs of the operation, since for the same length of the wound, several times the amount of suture material is needed compared to the continuous sewing method.

The sewing devices claimed in the U.S. patents are so bulky that it is impossible to apply continuous sutures and to obtain unobtrusive scars with them.

The suture material according to EP 1075843 is also fairly expensive—with a unit of such suture thread a wound of only 10 cm in length can be sewn up (else the removal of the thread after the healing of the wound becomes difficult), while sewing up wounds with conventional atraumatic smooth threads is possible for single cuts of 7-10 cm with the entire length of suture thread (approximately 45 cm).

According to EP 1 075 843, the amount, strength, and also the durability of the engagement of the seams of the second set with the tissues is insufficient for keeping the free end of the thread from slipping into the depth of the wound. At the same time, the strength and durability of the engagement of the seams of the first set with the tissues is abundant. The fact is that according to the invention each seam on the right and on the left has the same strength, and also the distance between them is equal. With each applied stitch, when the thread is tightened and the edges of the wound are crimped to some extent, the tension on the very first seam of the second set is gradually increased. At some point it will fail to stand this, will bend or tear, and the thread will slip into the depth of the wound in one turn. If the tension continues to increase, the same will happen to the second seam and so on, hence the end of the thread can slip under the skin. Even if that does not happen, the entire construction can still slacken at the instant when the operation is finished, and there is a risk that the suture turns out to be unstable.

According to EP 1 075 843 the conically shaped protrusions claimed in the invention do not reliably keep the tissues in a tightened state. The fact is that when the thread is tightened to the opposite side and the pressure on the protrusions is gradually increased, they will spread out, become arranged perpendicularly with respect to the thread and then bend, and the thread will slip into the tissue in one or several turns. That is, the protrusions on the threads, when a tightening is carried out, will not turn into hooks engaging the tissues, but will simply bend away, as is confirmed in the specification, and this is insufficient for a reliable fixation of the thread with the protrusions in the tissues. This is particularly important for the second group of seams.

In surgical practice there are cases when during the sewing up of a wound a considerable force is necessary for contracting the edges. Here, the surgeons have to carry out a wide mobilization of skin-fat patches from both sides of the wound, which is not always technically possible, and also apply a large number of multi-layer and frequent single sutures in the subcutaneous layers as well as on the skin. For wounds spreading over a large area, single sutures applied on the edges of the wound (especially on subcutaneous fat cell tissues) often get perforated, since with conventional suture needles it is impossible to keep a sufficient volume of tissue in the loop.

The wide mobilization of tissues, the application of a large number of sutures on the edge of the wound and the considerable tension of the skin around the edges of the wound results in additional traumatisation of the edges of the wound as well as of the adjacent portions, prolongs the process of healing of the wound, increases the risk that its edges spread out, and finally renders a rough broad scar.

The usage of double-pointed surgical needles (PCT/RU2004/000252 of Jun. 30, 2004) for tightening soft tissues showed that this suture material has some negative properties.

Although a sewn and tightened portion of flabby soft tissues without apparent cuts, without rough retractions of the skin, with an even, smooth contour is obtained, a relapse of deformations occurs fairly soon (after 4-10 months), and the patients are not satisfied with such short-lived results. The cause for this failure is that the threads used for sewing are smooth and the tissues tightened by them swiftly and easily slip away downwards.

The "APTOS" threads according to RU 2268752 (PCT/RU 02/00285) also have negative properties.

When they are used for tightening soft flabby tissues by the means claimed in the patent, the results of the operations are also short-lived. The fact is that the protrusions on the "APTOS" threads according to said patent are arranged so that in the tissues one half of them works against the other half. Irrespective of whether these protrusions are arranged opposite each other on the different halves of the thread (left or right of the centre of the length of the thread) or whether they alternate, their quantity and also the strength of each are occasionally insufficient for supporting the entire conglomerate of soft tissues.

Moreover, when the thread is not guided into the opening of the needle carefully, the protrusions (especially those which point to the side of the movement of the thread) can bend and not spread out in the tissues, which causes a one-sided weakening of the thread engagement.

The weakness of the protrusion is explained by the shortcoming of its design, and the insufficient quantity is explained by the fact that the protrusions tighten the ptotic tissues only on one half of the length of the thread, while the protrusions of the other half fixate and support the protrusions of the first half.

Considering these shortcomings of employed suture materials and methods of their use, it is expedient to employ a new, more effective surgical material with protrusions on the threads, with the help of which a more reliable sewing of operation wounds with a continuous cosmetic suture is possible, to apply a new, more effective method of contracting the edges of such operation wounds, which require a considerable force for doing so, and to employ a new surgical suture material, which allows a combination of the possibilities of the method of internally sewing soft tissues with the aid of double-pointed needles and the methods of tightening with "APTOS" threads and protrusions, to suggest new and effective operations for tightening ptotic tissues of the face, the body and the extremities.

SUMMARY OF THE INVENTION

To eliminate the mentioned shortcomings of the suture materials and methods of their application, a series of versions of new surgical suture materials and methods of their application in chirurgical and plastic surgery is suggested.

The suture material comprises a needle of metallic, polymer or organic materials and a thread of the same materials with protrusions on the surface, characterised in that the needle is composed of two needles which are temporarily affixed to one another, forming a single needle of a four-sided, rhomboid or other shape, and, when affixed, forming one point, the ends of the thread being attached to the different needles opposite to the point in such a way that the protrusions of the shaped design on the thread are arranged from opposite sides of the latter from the centre of the thread with their ends opposite to the attachment of the thread in the needles.

Another version of the suture material is characterised in that the needle is a double-pointed composition, and the thread is fixed by its ends to the central part of the needles at a distance from the points of the needles, the protrusions of the shaped design being directed with their ends opposite to the attachment of the thread in the needles.

The next version of the suture material is characterised in that the needle is double-pointed with a thread, the ends of which are attached to the needles directly at one of the sharp ends.

Another suture material is characterised in that it consists of a double-pointed needle with a thread with protrusions of a shaped design.

The next version of the suture material comprising a thread is characterised in that the thread comprises protrusions, applied with the aid of notches, having a length of approximately 1.5 to 5 times the diameters of the thread with a shaped design of the variable cross-section, amounting at the basis to approximately ¼ of the diameter of the thread from the surface and at the central part to approximately ⅓ of the diameter of the thread from the surface with a gradual transformation to the sharpened end of the protrusion, which allows a bending of the protrusion in the form of a fishing hook when the thread is pulled back in the process of sewing soft tissues.

The surgery is carried out with the following methods. In the method of applying the suture material for sewing up the edges of wounds requiring forces for contracting the edges of the wounds, the double-pointed needle with the thread with the inclined protrusions of the shaped design is introduced with either point into one of the wound edges up to a predetermined depth, thereafter the needle with the thread is moved parallel to the skin perpendicularly to the wound edge to the necessary distance from the wound edge, subsequently the point is directed to the surface of the skin but not extracted entirely, the second point remaining approximately at the depth of the passage of the thread, and, rotating the needle by an angle of 90°, a rectangular stitch is continued to be made, thereafter the same is done on the other edge of the wound, the ends of the thread being connected to each other.

The quantity of applied stitches is determined by the necessity of rendering a reliable fixation of the wound edges and a sufficient contracting thereof.

The method of sewing up the edges of a wound with suture material in a continuous cosmetic suture is carried out as follows: The needle is inserted at one of the edges of the wound approximately one centimeter away from the end of the wound, and the point of the needle is inserted into the subcutaneous cellular tissue of the wound by a known method, continuous stitches are applied in turns to each of the wound edges, gradually moving to the opposite end of the wound, wherein with each stitch the thread is tightened with some excess amount of force, which also results in a contraction of the wound edges and some weakly delineated perforation of the tissues, after the sewing of the wound is terminated, the needle is extracted at the opposite end on the surface of the skin, if necessary, the thread is additionally tensioned and trimmed, leaving a portion of at least three centimetres of the thread above the skin.

The operation of tightening ptotic tissues in the cheek and cheekbone area of the face consists of the following steps: a localized punctuation is made, the needle is inserted into the subcutaneous tissues to the required depth, thereafter the needle is divided in two, and further each needle is led along its contour, and when they are rotated, they are not fully extracted to the surface, they are rotated and continue the subsequent movement with the other point of the needle along the other contour, whereby the tissues are tightened. The extraction of the needles is implemented at the point of the initial puncture, where the thread is also fixed. This manipulation allows quality surgery. At the positions where the thread is bent, the skin is not pulled in—the bend of the thread is located subcutaneous to the level where the needles were separated.

BRIEF DESCRIPTION OF THE DRAWINGS

Below, the suggested invention is explained by drawings.

DETAILED DESCRIPTION

The surgical suture material and the method of its usage are presented in various versions of the needle and thread for carrying out surgical and cosmetic operations.

In FIGS. 1, 2, 3, and 4, elements of the surgical thread are shown. The thread 1 is manufactured from a metallic, polymer, or organic material with complex protrusions on the surfaces of two sets, the ends of the first set 2 being directed against the tightening direction of the thread. The first set of protrusions is situated in the tissues and is responsible for a quality contraction of the wound edges, while the second set 3 is directed in the tightening direction of the thread. The second set is situated above the skin and is necessary to counteract a slipping of the thread.

Figures 3, 4:
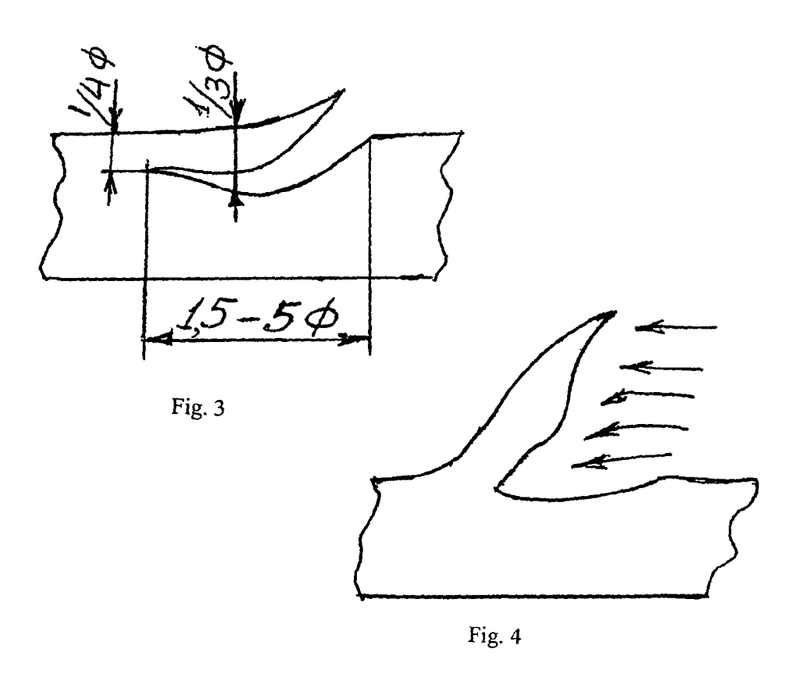
FIG. 3 shows a complex design of the protrusions in the shape of notches.
FIG. 4 schematically shows the form of the protrusion in the shape of a notch subjected to the pressure of the tissue.

FIG. 4 schematically shows the effect of the force of the tissues on the shaped protrusions. To carry out the intended functions, a series of versions of needles and threads usable in surgery and making up the suture material is explained.

Figure 1:
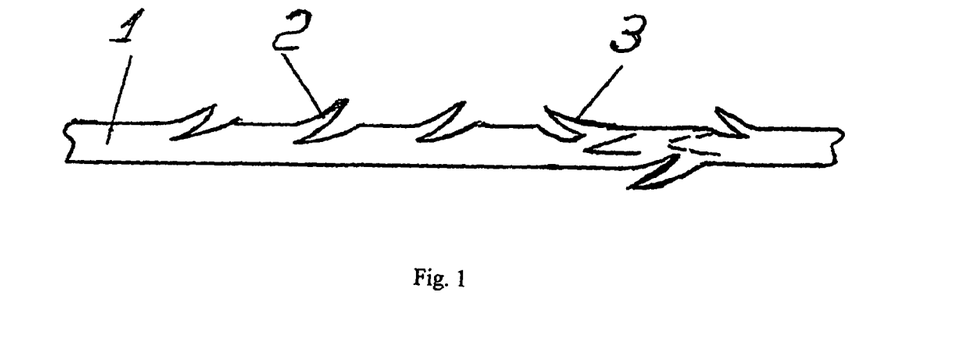
FIG. 1 shows a thread with protrusions of the first and second order.
Figure 2:
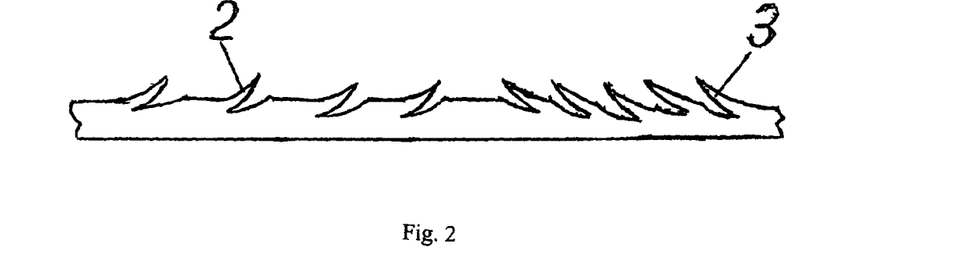
FIG. 2 shows a thread with protrusions of the first and second order, arranged on one side of the thread.
Figure 5:
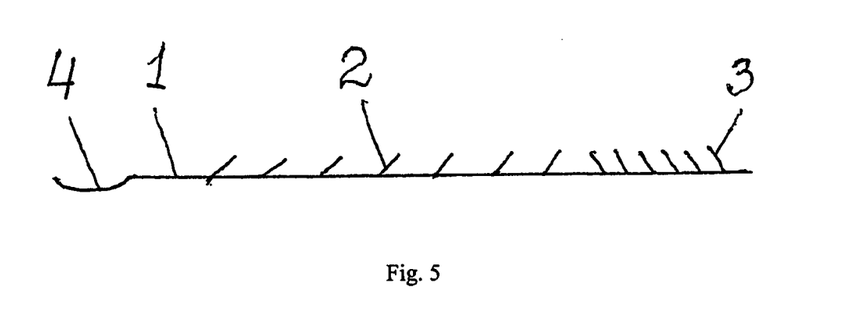
FIG. 5 shows a recommended thread for sewing a wound by the continuous technique.

In FIG. 5, the thread 1 with the needle 4 for sewing up the wound with a continuous suture is shown in analogy to FIGS. 1 and 2. The thread comprises protrusions 2 and 3 of a shaped design.

Figure 6:
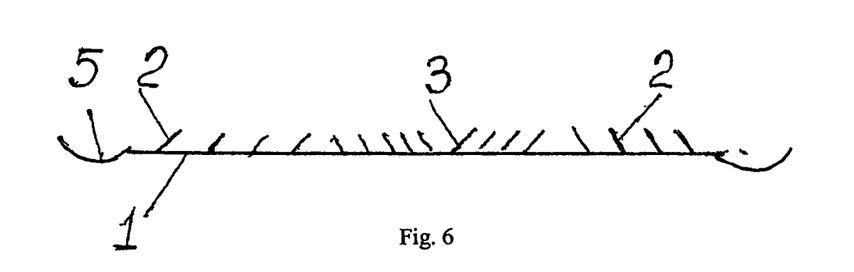
FIG. 6 shows a thread for sewing one wound in two stages.

FIG. 6 shows an analogous version of the thread 1 with two needles 5 and protrusions 2 and 3 with a shaped design. This thread is a double one which can be divided into two individual ones for operations.

Figure 10:
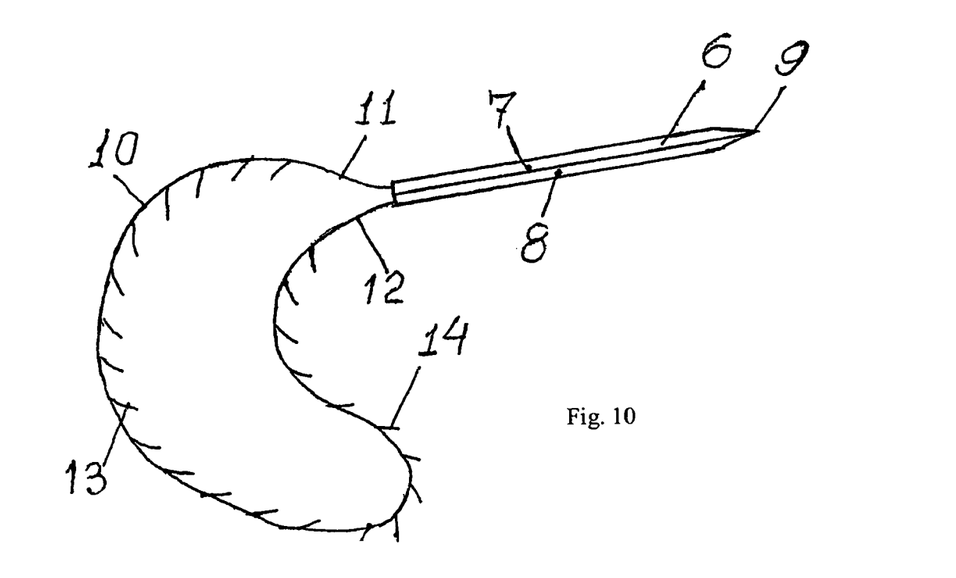
FIG. 10 shows a suture material with a double needle used for tightening soft tissues.

The most distinctive representation is the one in FIG. 10. It comprises a needle 6 being temporarily combined from two needles 7 and 8 forming a single needle with a single point 9. The shape of the combined needle can be four-sided, rhomboid or of another form in cross-section. The thread 10 is attached by its ends 11 and 12 to the needles 7 and 8, while the protrusions of shaped design 13 and 14 are provided on the thread from opposite sides from the centre of the thread and directed with their ends opposite to their attachment in the needles.

The use of duplex needles when carrying out surgical and cosmetic operations allows to reach a new quality. With the needle 6 a single subcutaneous puncture is made, which is deepened to the required depth, subsequently the needles 7 and 8 are divided and each is directed along a different contour, after the needles puncture the marked points, e.g. the points where they were introduced, and the threads are tightened, the bends of the threads are sunk under the skin to the level where the needles were divided.

Figure 11:
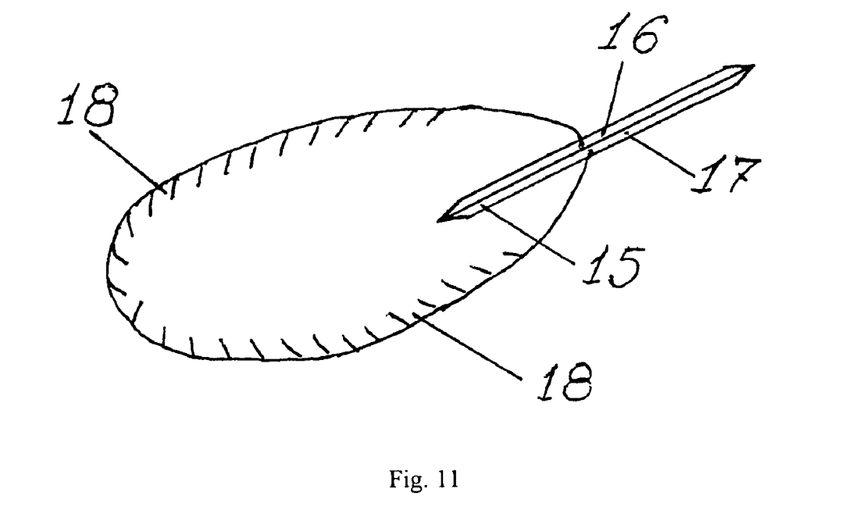
FIG. 11 shows a suture material with a double double-pointed needle.
Figure 17:
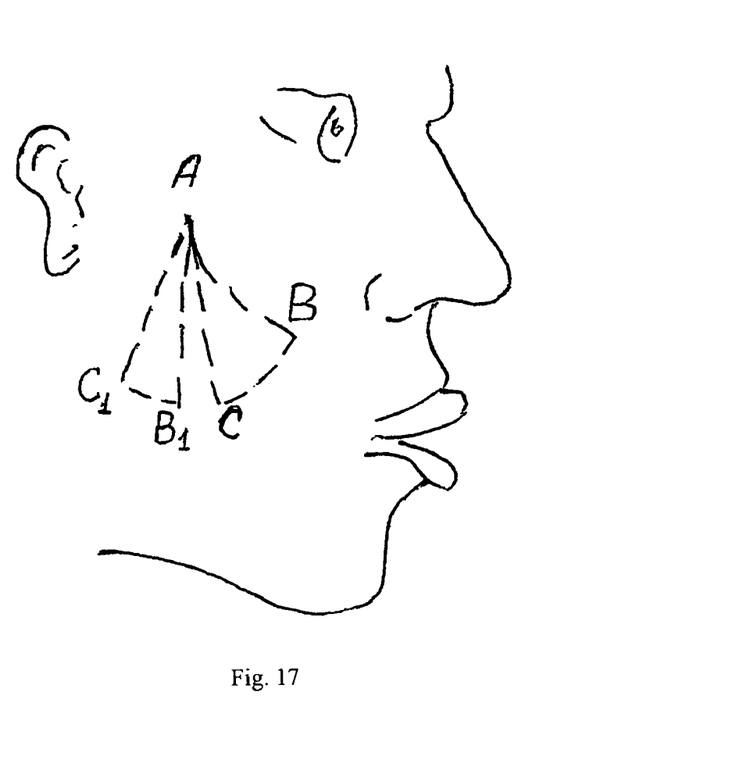
FIG. 17 schematically shows the tightening of tissues in the cheek and cheekbone area using a duplex needle.

Another version of the application of the suture material is shown in FIG. 11. The double-pointed needle 15 made up of the needles 16 and 17 makes a single puncture at the point "A" (see FIG. 17) in the upper part of the cheekbone area, the thread 18 attached to the needle 16 with the shaped protrusions is directed along the triangular contour "A", "B", "C", while the needle 15 with the second half of the thread 18 is directed along a different contour "$A_1$", "$B_1$", "$C_1$" with the punctures and bends of the needles. The protrusions of the shaped design are bent, embedded in the donor stock of the thread, from where they are cut out, and after the needles return and are extracted at the point "A" and after the knot is tied, the tissues are firmly fixed in the new elevated position.

The sewing of the soft tissues with a double-pointed needle with protrusions on the threads is more reliable than a tightening with smooth threads, since the tissues are evenly distributed and fixed along the length of the thread, do not sag and do not slip thereon in the course of time.

As a version of the corresponding suture material, a thread has shaped protrusions arranged opposite one another along its entire extension. In this case the thread is arranged in a flexible tube e.g. of cellophane, which is extracted from the thread canal after the operation. As a version, the thread can be covered with resorptive material.

Figure 7:
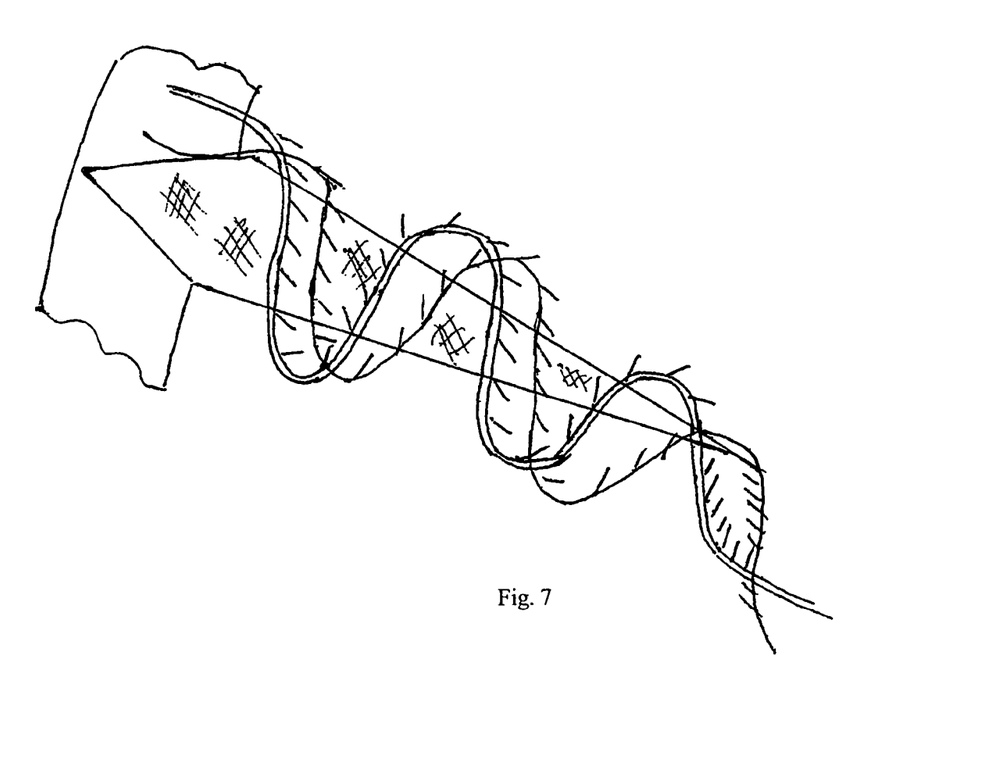
FIG. 7 shows the sewing of a wound with two threads on different levels.
Figure 8:
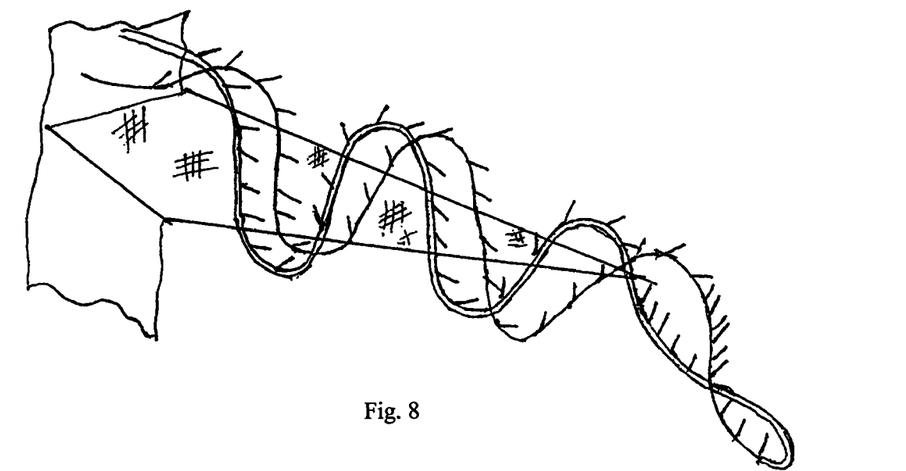
FIG. 8 shows the sewing of a wound with one thread on different levels.
Figure 9:
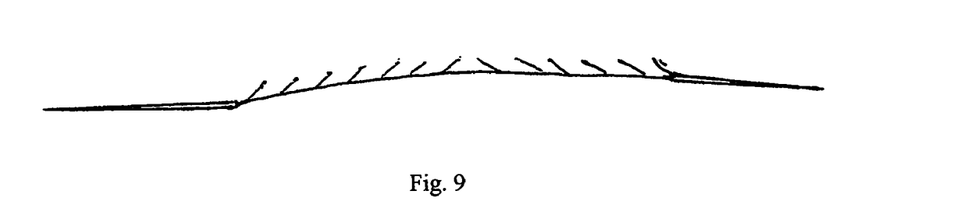
FIG. 9 shows a thread with protrusions in the shape of notches of a shaped design provided with two needles for tightening soft tissues.

In FIGS. 7 and 8, versions of the sewing of a wound with threads on two levels are shown. One version (FIG. 7) comprises two threads, the second version—FIG. 8—comprises one thread with different directions of the shaped protrusions.

Figure 12:
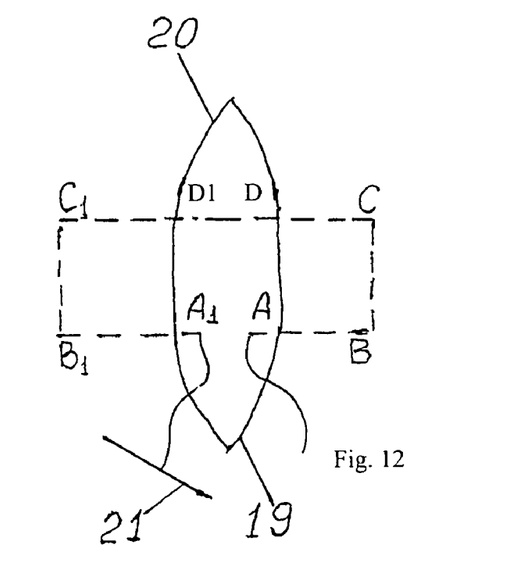
FIG. 12 shows a scheme for sewing the edges of a wound with rectangular stitches requiring large forces.
Figure 13:
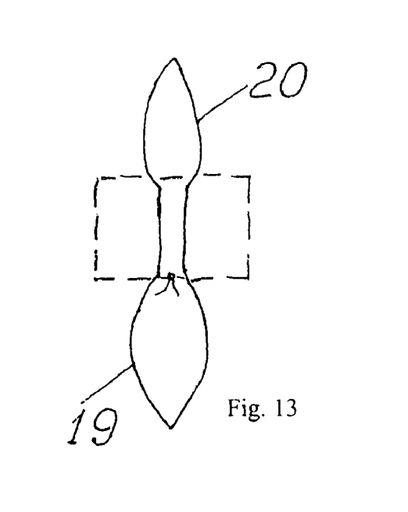
FIG. 13 shows the edges of the wound tightened with rectangular sutures.
Figure 14:
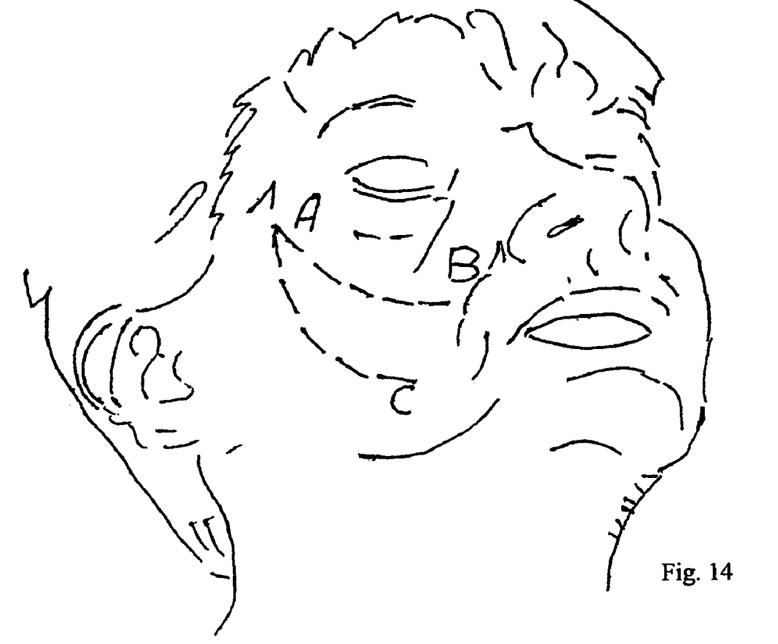
FIG. 14 schematically shows the tightening of soft tissues in the cheek and cheekbone area.
Figure 15:
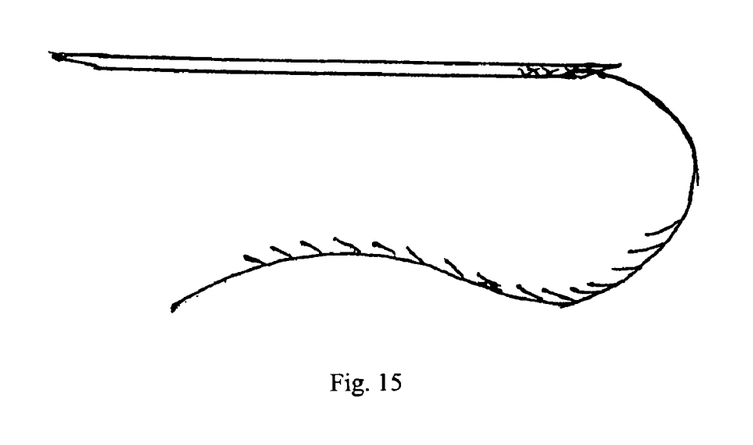
FIG. 15 shows a double-pointed needle with a thread attached immediately to one of its ends.
Figure 16:
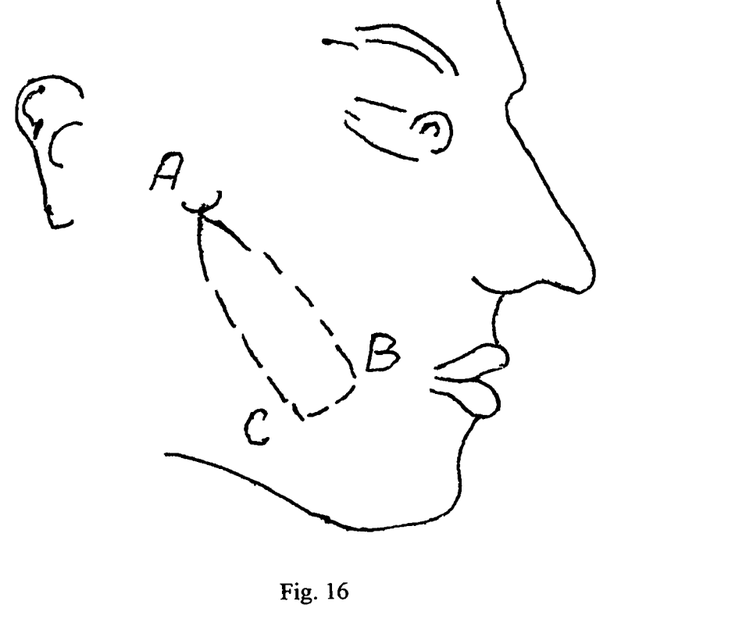
FIG. 16 shows the tightening of tissues in the cheek area.

Another version of the application of the suture material (see FIGS. 12 and 13). The operation is carried out as follows. This method is used for sewing up wounds requiring forces for contracting the edges of a wound 19 and 20, the double-pointed needle 21 with the thread with the bent protrusions of the shaped design is inserted by either point to a predetermined depth into one of the edges of the wound, subsequently the needle 21 with the thread is moved parallel to the skin perpendicularly to the edge of the wound at an indefinite distance from the edge of the wound, further the point is directed to the surface of the skin but not extracted entirely, leaving the second point approximately at the depth of the passage of the thread, and rotating the needle by an angle of 90°, the rectangular stitch is continued, thereafter the same is carried out at the other edge of the wound, the ends of the thread are joined to one another.

As shown in the description, the suggested invention can be widely used in a variety of cosmetic and surgical operations, and also in combination with other surgical interventions.

The suggested surgical suture material is feasible and can be applied widely.

The invention claimed is:

1. Method for applying a surgical suture material comprising a needle and a thread made of a material selected from the group consisting of metallic, polymer and organic materials, the thread is formed with protrusions on a surface, the needle is composed of two needles which are temporarily affixed to one another, forming a single needle of a shape selected from the group consisting of four-sided, rhomboid and other shape in cross-section, the two needles forming a united pointed end when affixed, ends of the thread are attached to a different needle, wherein the protrusions on the thread have a shaped design along an axis and are arranged on opposite sides thereof from a center, the ends of the protrusion are directed opposite to the attachment of the thread in the needles for a cosmetic facelift for soft tissues in the cheek and cheekbone area of the face, the method comprises the steps of making a localized punctuation wherein the needle is inserted into subcutaneous tissues to a required depth, thereafter dividing the needle in two, and leading each needle along its contour, and when the needles are rotated, they are not fully extracted to the surface of the skin, they are rotated and continue the subsequent movement with the other point of the needle along the other contour, whereby the tissues are tightened, wherein the extraction of the needles is implemented at the point of the initial puncture, where the thread is also fixed.

* * * * *